United States Patent [19]

Nicholas et al.

[11] Patent Number: 5,431,675
[45] Date of Patent: Jul. 11, 1995

[54] LOCKING MECHANISM FOR ENDOSCOPIC OR LAPAROSCOPIC SURGICAL INSTRUMENTS

[75] Inventors: David A. Nicholas, Trumbull; David T. Green, Westport; Henry Bolanos, East Norwalk; H. Jonathan Tovey, Milford; Paul O. Rawson, Easton, all of Conn.

[73] Assignee: United States Surgical Corporation, Norwalk, Conn.

[21] Appl. No.: 323,419

[22] Filed: Oct. 13, 1994

Related U.S. Application Data

[63] Continuation of Ser. No. 949,686, Sep. 23, 1992, abandoned.

[51] Int. Cl.⁶ .............................................. A61B 17/32
[52] U.S. Cl. .................................. 606/170; 606/206; 606/208
[58] Field of Search ................. 606/46, 167, 170, 205, 606/206, 208

[56] References Cited

U.S. PATENT DOCUMENTS

| | | |
|---|---|---|
| 253,209 | 2/1882 | Jones . |
| 1,266,456 | 5/1918 | Greeley . |
| 1,327,577 | 1/1920 | Turner . |
| 2,597,394 | 5/1952 | Snowden . |
| 2,652,832 | 9/1953 | Castroviejo . |
| 2,706,987 | 4/1955 | Bramstedt . |
| 2,795,225 | 6/1957 | Sovatkin et al. . |
| 3,270,745 | 9/1966 | Wood . |
| 3,326,216 | 6/1967 | Wood . |
| 3,995,619 | 12/1976 | Glatzer . |
| 4,282,884 | 8/1981 | Boebel . |
| 4,392,494 | 7/1983 | Ashby . |
| 4,414,908 | 11/1983 | Eguchi et al. . |
| 4,491,135 | 1/1985 | Klein . |
| 4,572,185 | 2/1986 | Rich . |
| 4,662,371 | 5/1987 | Whipple et al. ...................... 606/170 |
| 4,753,235 | 6/1988 | Hasson . |
| 4,760,848 | 8/1988 | Hasson . |
| 4,815,460 | 3/1989 | Porat et al. . |
| 4,817,847 | 4/1989 | Redtenbacher et al. . |
| 4,836,205 | 6/1989 | Barrett . |
| 4,848,367 | 7/1989 | Avant et al. . |
| 4,873,977 | 10/1989 | Avant et al. . |
| 4,898,157 | 2/1990 | Messroghli et al. . |
| 4,961,742 | 10/1990 | Torre . |
| 5,184,625 | 2/1993 | Cottone, Jr. et al. . |
| 5,190,549 | 3/1993 | Miller et al. . |
| 5,235,966 | 8/1993 | Jamner ............................... 606/208 |

FOREIGN PATENT DOCUMENTS

| | | |
|---|---|---|
| 357377 | 8/1989 | European Pat. Off. . |
| 2708830 | 9/1978 | Germany . |
| 772132 | 1/1955 | United Kingdom . |
| 2146900 | 9/1983 | United Kingdom . |

Primary Examiner—C. Fred Rosenbaum
Assistant Examiner—N. Kent Gring

[57] ABSTRACT

A surgical instrument according to an embodiment of the present invention includes a housing portion and an endoscopic portion having a proximal end and a distal end, the endoscopic portion including a pair of coaxial members attached at the proximal end to the housing portion. The endoscopic portion also includes an inner rod member slidable within an outer tube member. The endoscopic portion terminates at the distal end in a pair of jaw members disposed in opposing relation and relatively pivotal about a common point between at least an open position and a closed position. A jaw control mechanism is associated with the housing portion, and includes at least one actuating member movably mounted in the housing portion. The actuation member has at least one gripping portion thereon such that an operator of the instrument can better manipulate the actuating member with a single hand. A linking member is pivotally connected to the actuating member and the inner rod member. A notch portion is disposed on the rod member such that when the actuating member is moved in relation to the housing portion in a first direction to a first position the engaging portion engages the notch, locking the jaws in a closed position. The surgical instrument also includes means for preventing the inner rod member from moving from the first position whereby coaxial reciprocating forces are created in the inner rod member when the locking means are moved to the first position.

55 Claims, 13 Drawing Sheets

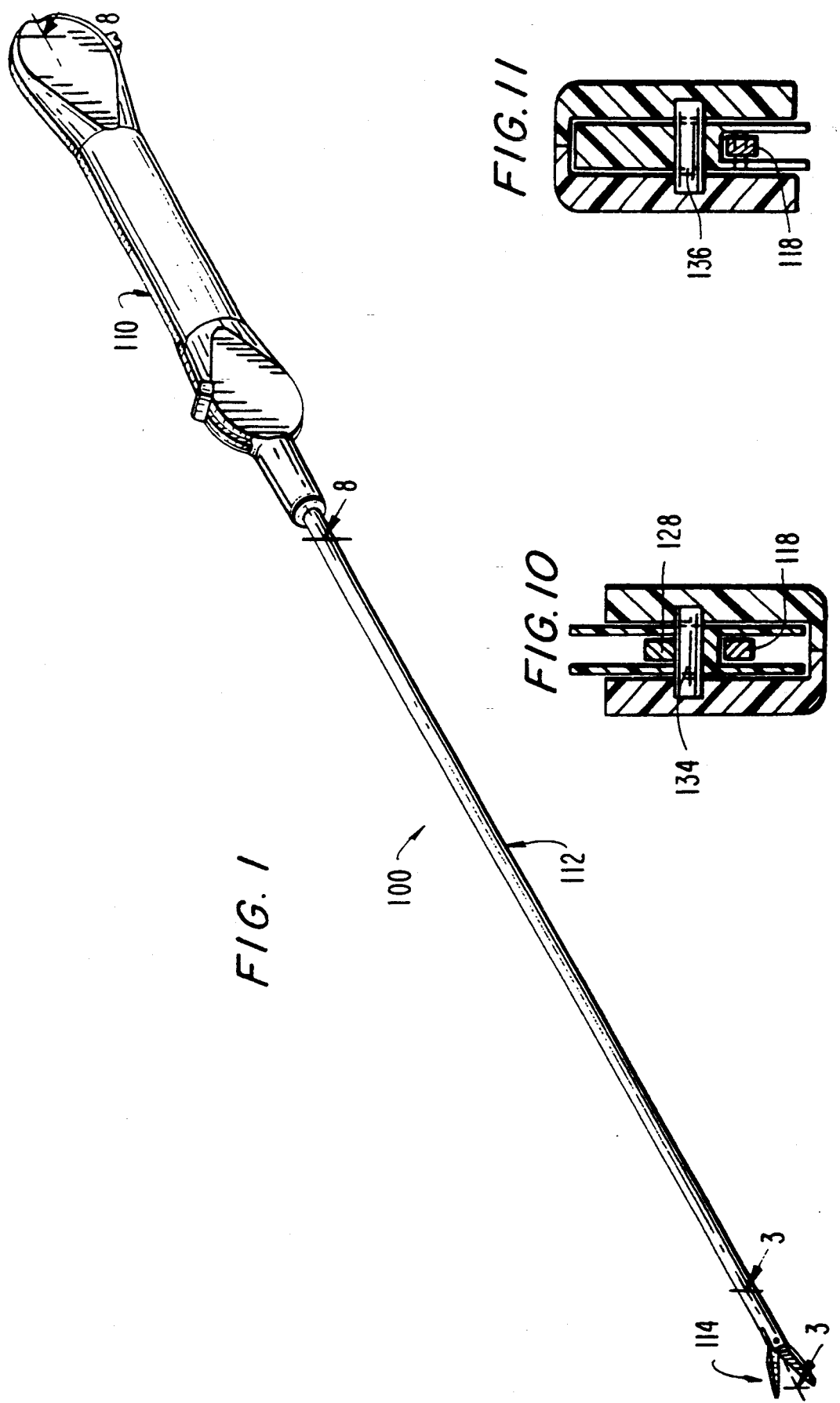

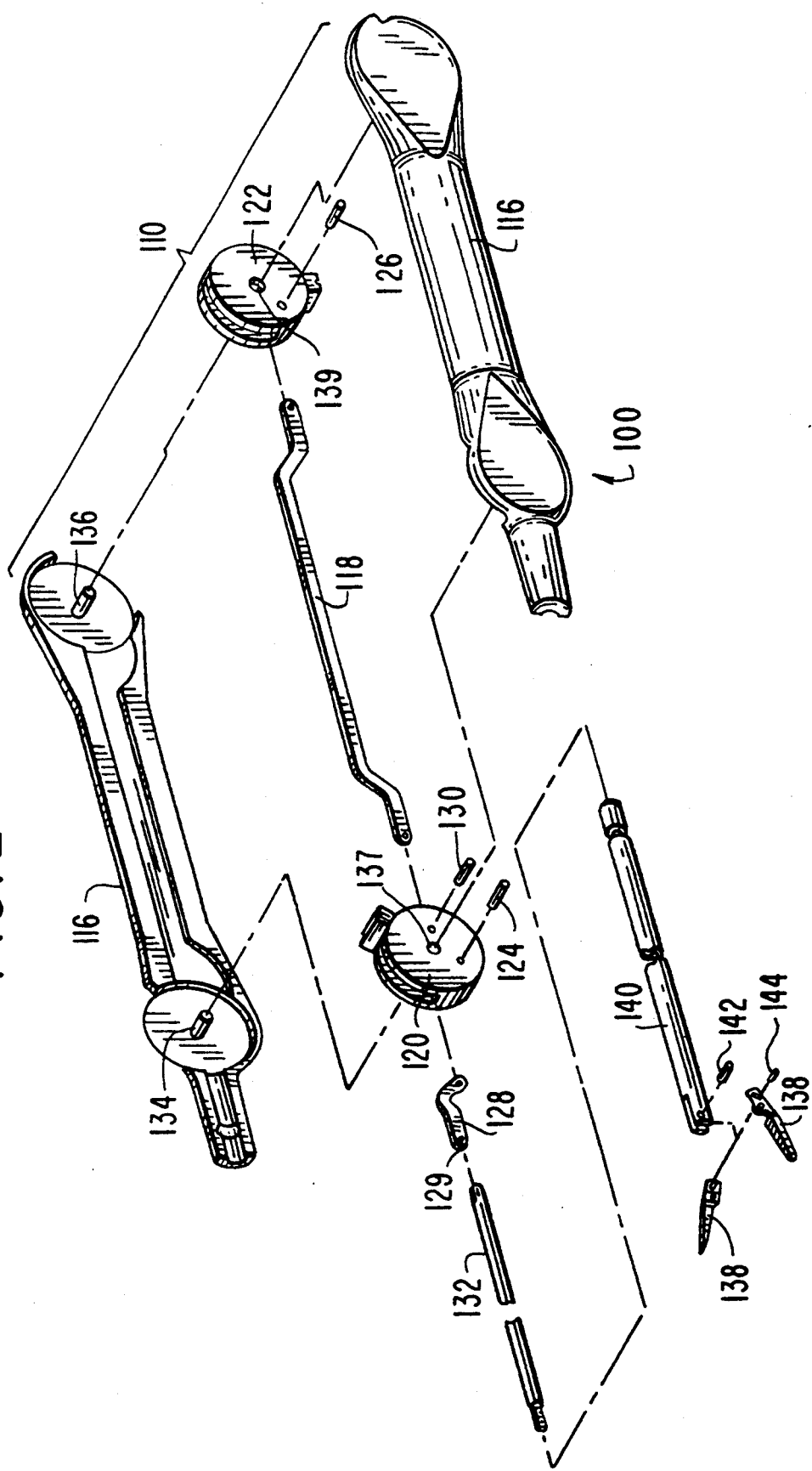

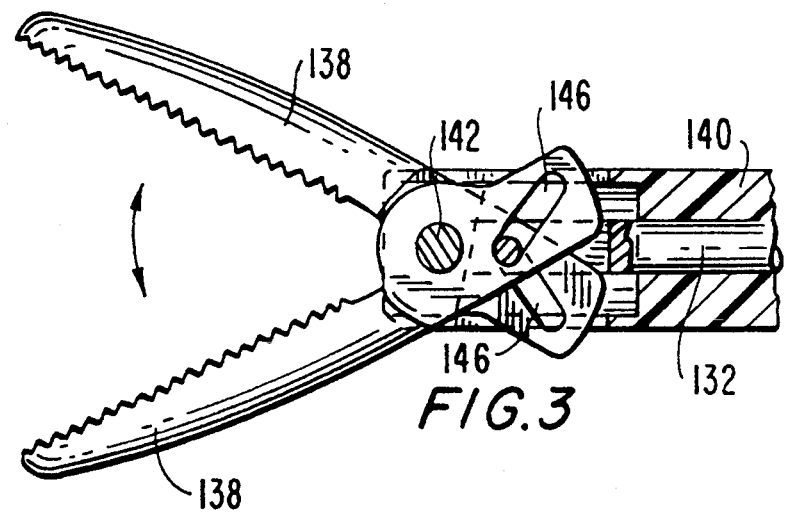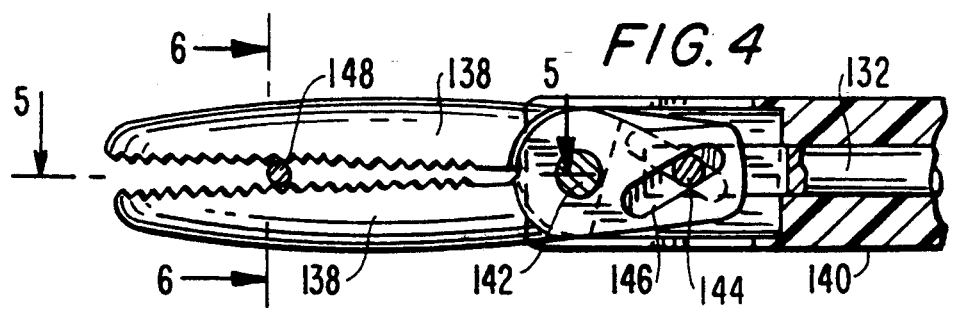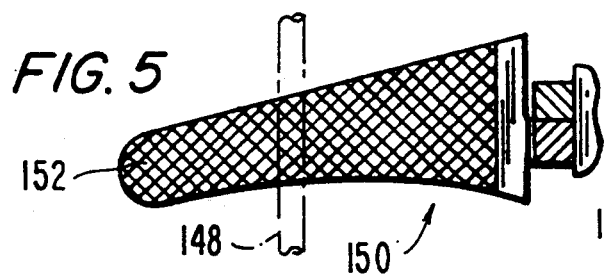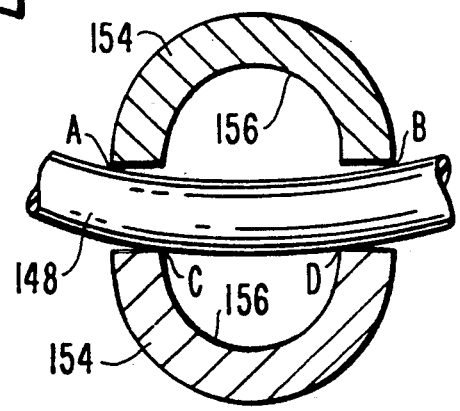

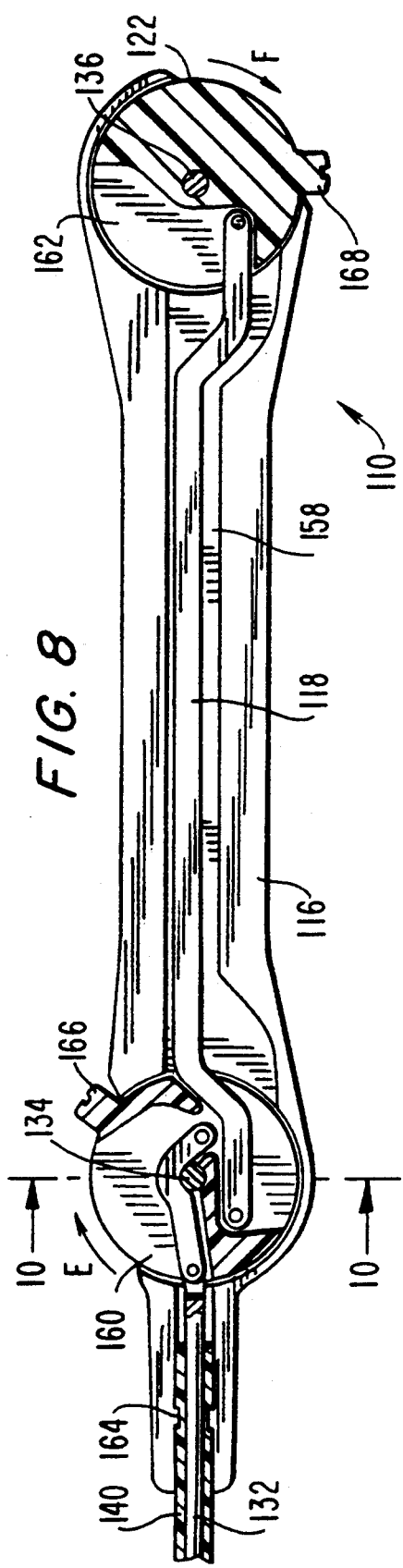
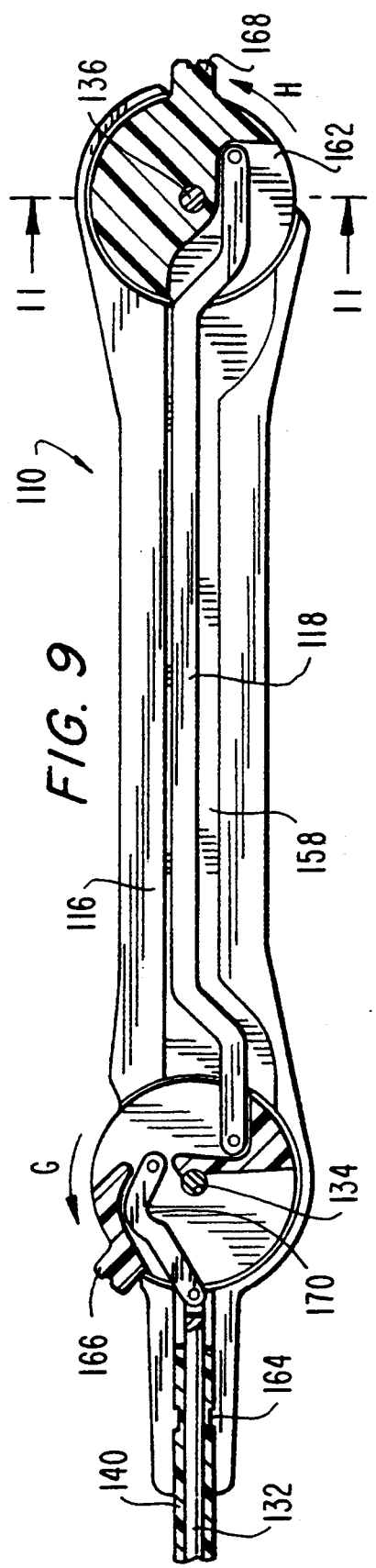

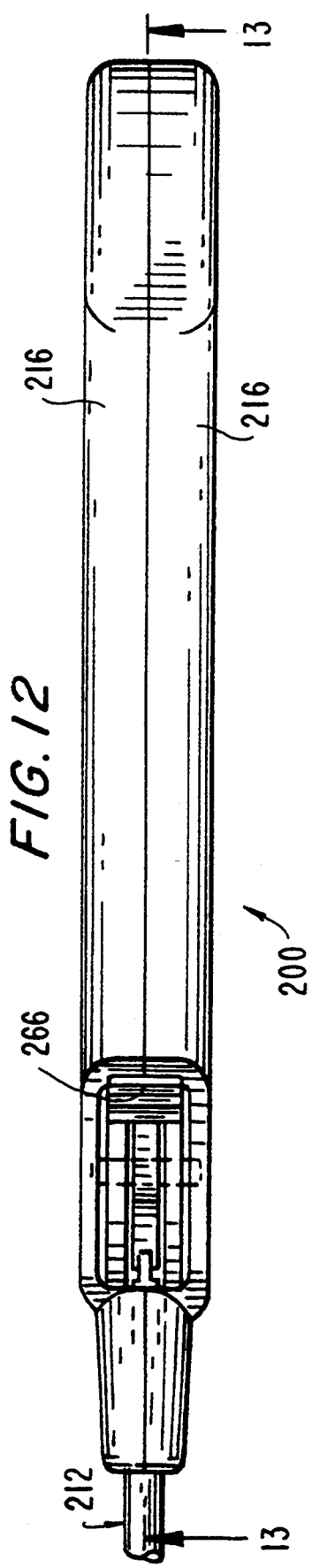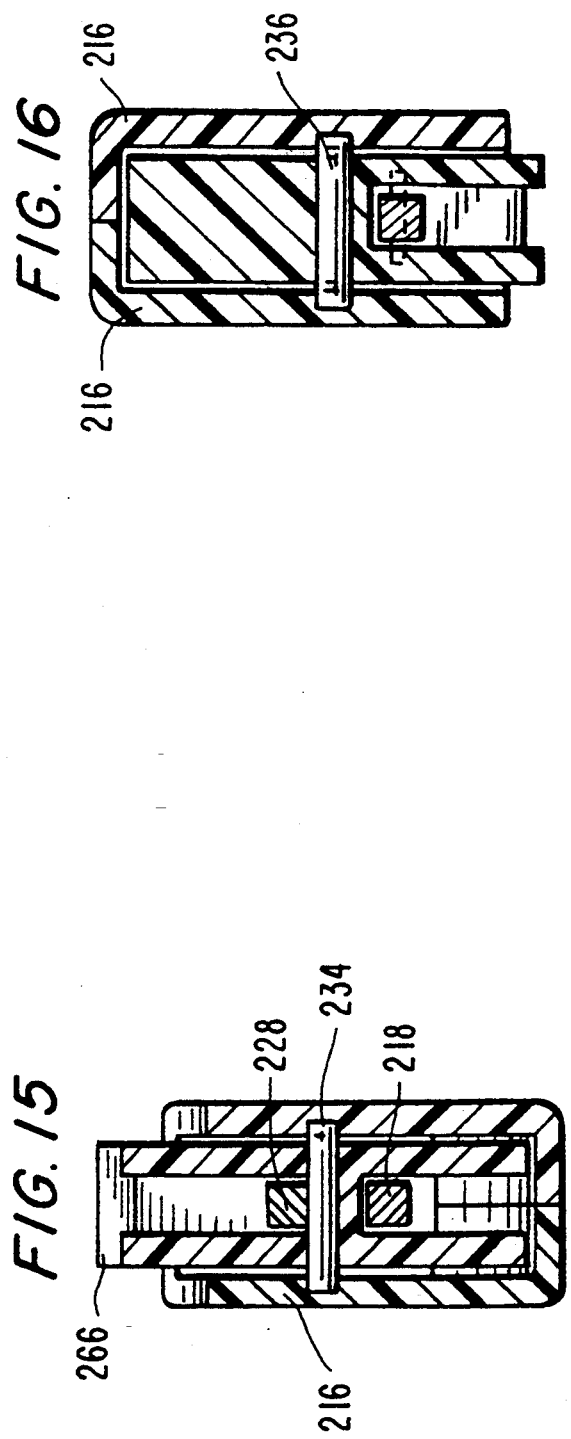

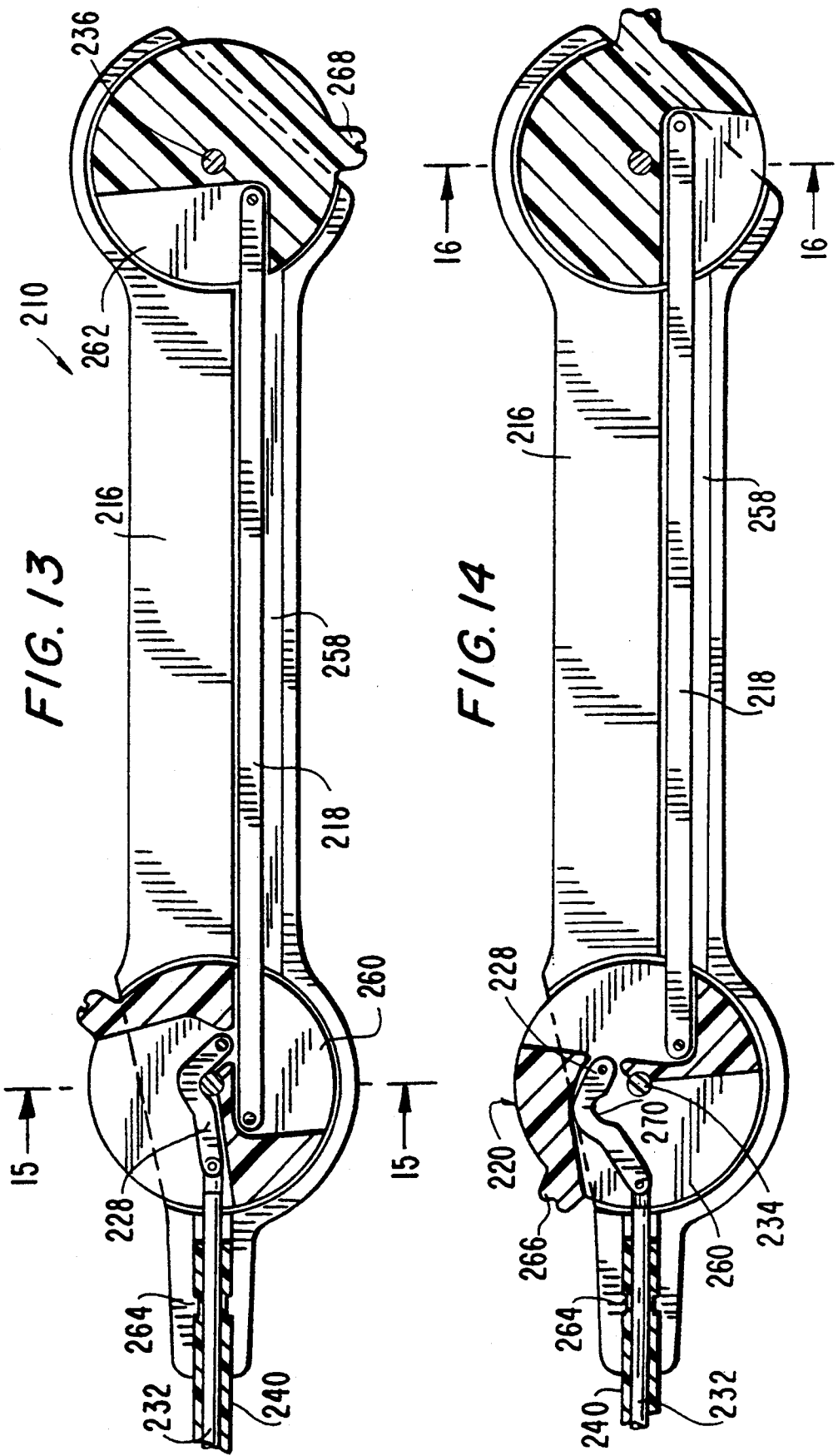

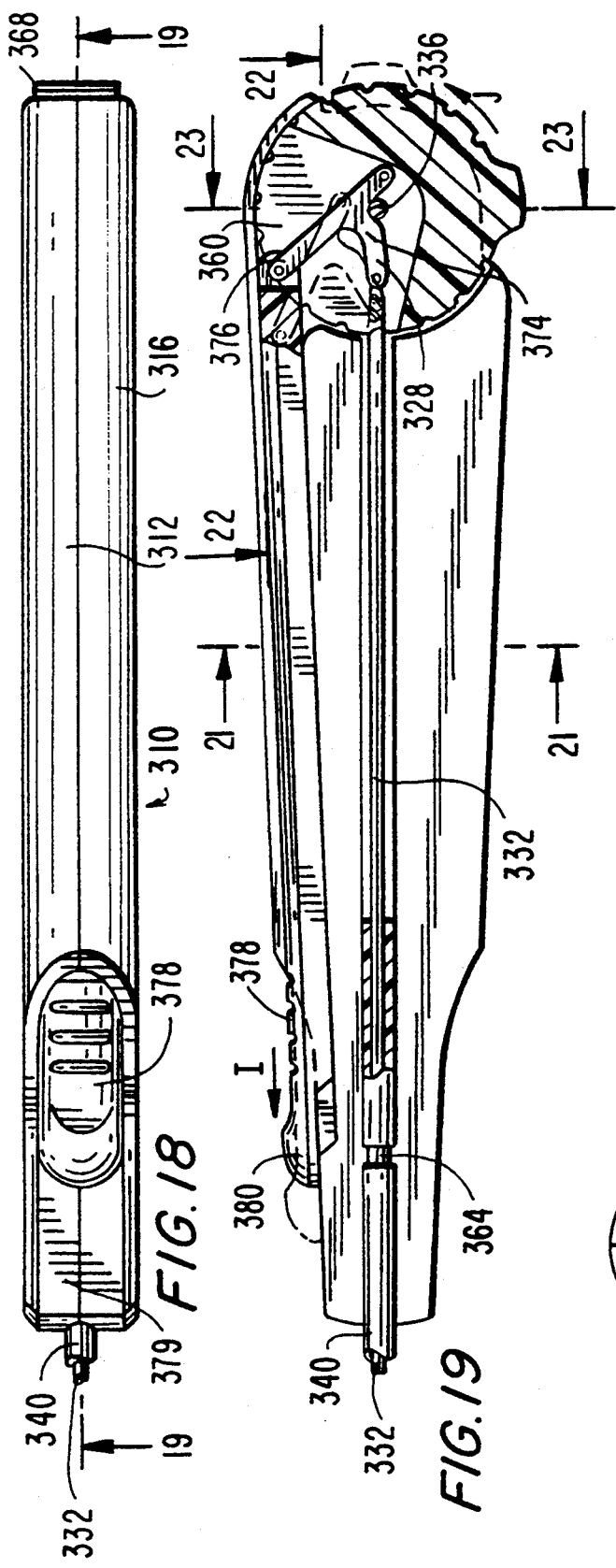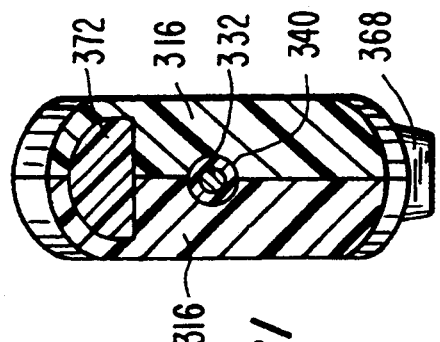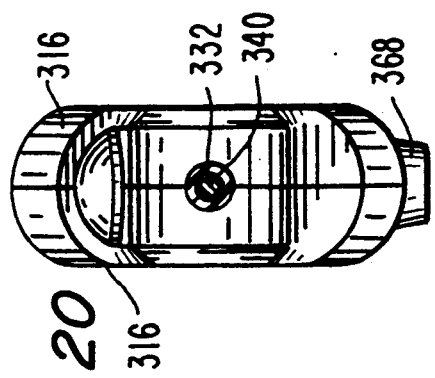

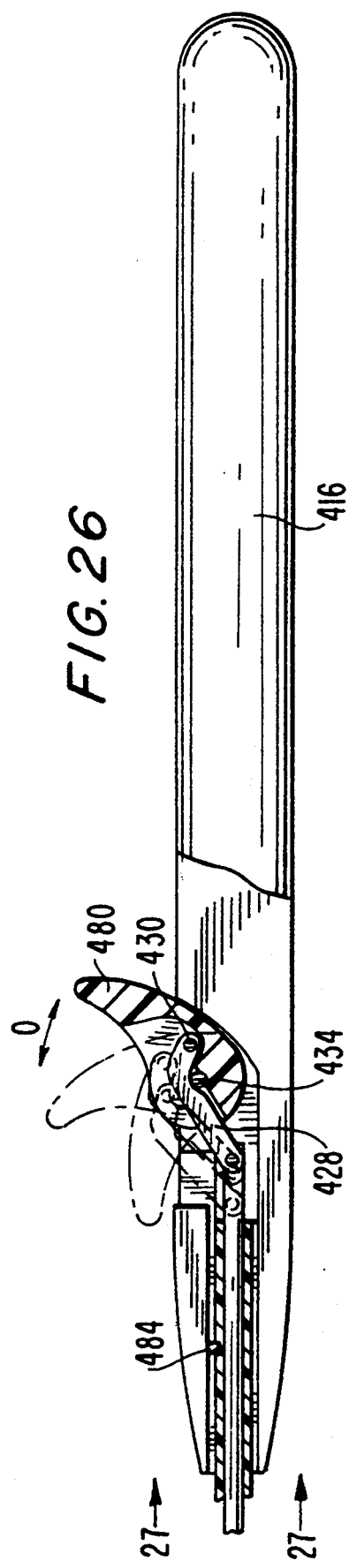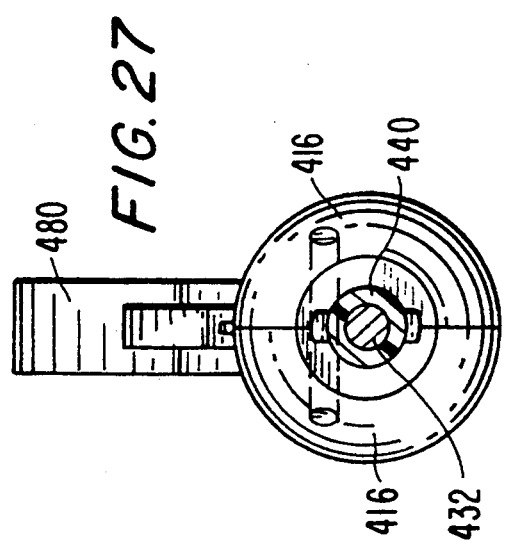

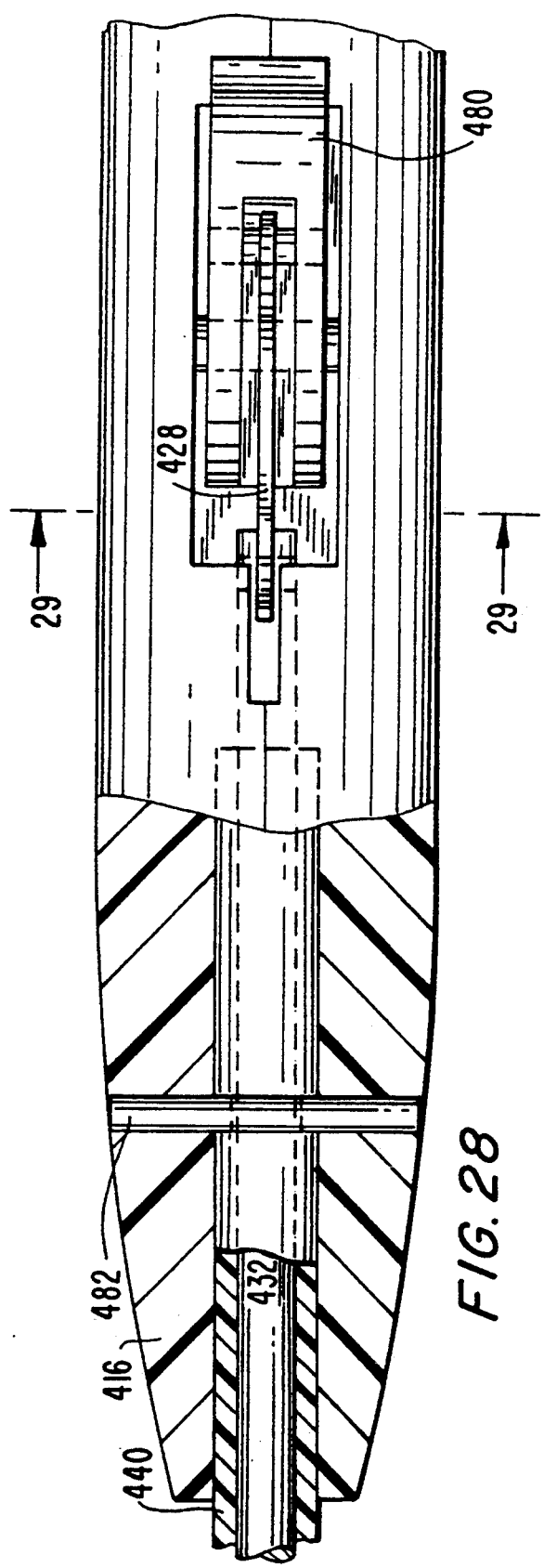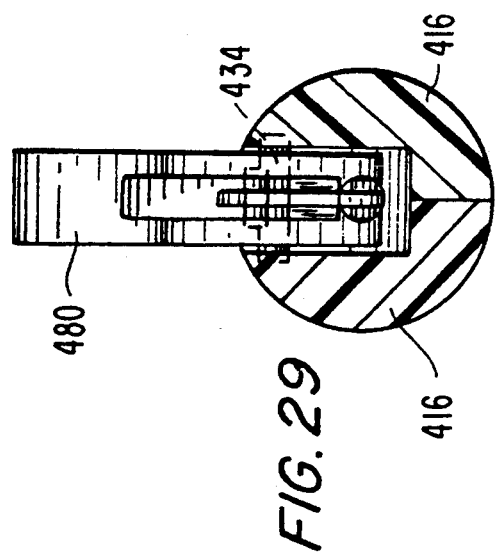

LOCKING MECHANISM FOR ENDOSCOPIC OR LAPAROSCOPIC SURGICAL INSTRUMENTS

This is a continuation of U.S. application Ser. No. 07/949,686 filed Sep. 23, 1992 now abandoned.

BACKGROUND OF THE INVENTION

1. Field of the Invention

The present invention relates to surgical instruments. More particularly, the invention relates to handles for endoscopic or laparoscopic surgical instruments having a novel locking mechanism disposed within the handle to provide for positioning and locking of a tool member of the instrument.

2. Discussion Of the Related Art

Endoscopic surgical procedures are procedures performed in any hollow viscus of the body through narrow endoscopic tubes which are inserted through small entrance wounds in the skin. Laparoscopic surgical procedures are endoscopic procedures in which surgery is performed in the abdominal cavity through small incisions. Endoscopic and laparoscopic procedures generally require that any instrumentation inserted into the body be sealed, i.e., provisions must be made to ensure that gases, used to insufflate the surgical region, do not exit the body through the endoscopic or laparoscopic incision or instrument. Moreover, endoscopic and laparoscopic procedures often require the surgeon to act on organs, tissues and vessels far removed from the incision, thereby requiring that any instruments be used in such procedures be long and narrow while being functionally controllable from one end of the instrument, i.e., the proximal end. For purposes of clarity, the remainder of the following discussion will refer to endoscopic procedures and instruments used therefor. It is to be understood, however, that the present invention is also meant to be applicable in laparoscopic procedures as well as any other applicable procedure requiring precision control and/or locking of a tool mechanism.

Various endoscopic surgical instruments which utilize generally complex tool and jaw actuating mechanisms in order to facilitate use of the devices at a surgical site exist in the art. Many such devices provide an intricate construction in which a linkage mechanism for opening and closing the tool mechanism or jaws requires numerous moving parts, while a sliding arrangement is provided between two extended rod members to activate the linkage mechanism in response to movement of the handle members. It is often necessary in many of these devices for the surgeon, or an assistant, to maintain a constant force on the handles in order to keep the tool or jaw mechanism closed. This is particularly true for instruments such as grasping or gripping devices including forceps, needle holders, or retractors. Constraints such as these limit the surgeon's flexibility and often require additional personnel to be present in the operating room to assist in handling the instruments, thus restricting movement in an already confined location.

To alleviate the above problem, attempts have been made to provide locking mechanisms on the handles of the surgical instruments which allow surgeons to lock and/or clamp the jaw members in place. These locking mechanisms allow the surgeon or the surgical assistant to use their hands for other more necessary functions. Typically such locking devices include arm members which extend between scissor-type handles so that a series of ridges or ribs on each arm member engage corresponding ridges on the opposite arm to lock the handles in position. Bending one arm in relation to the other releases the locking mechanism.

One disadvantage associated with these devices concerns the release of the locking mechanism for subsequent movement of the jaw members to remove or reposition the instrument. Generally, the arm members of locking mechanisms are constructed of a resilient material, such as stainless steel or rigid plastic, and the locking forces which hold the arm members in engagement are generated by the natural flexing and biasing of the material from which the arm members are constructed. To release the locking mechanism, the arms must be disengaged by overcoming the locking forces of the arms. Typically, this is accomplished by manually flexing the arms away from each other, necessitating the use of two hands, one to grasp the instrument, and the other to forcibly move the arm members.

Another disadvantage with locking mechanisms located on the handles is that they require special care in sterilization, packaging and storage, as well as in normal handling in the operation room. Dirt and debris may clog the fibs of the locking mechanism thus reducing its effectiveness, and damage to the fibs during storage or packaging may disable the fibs, rendering the locking mechanism useless.

U.S. Pat. No. 1,452,373, to Gomez discloses a typical locking mechanism for a surgical instrument in which a plurality of ribs are provided on an extension of the handle member which engage a similar rib member on the opposite handle. Once engaged, the handles must be moved away from each other perpendicular to their longitudinal axis to disengage the locking mechanism to release the jaw mechanism.

U.S. Pat. No. 4,896,661, to Bogert et al. discloses a surgical instrument having a ratchet mechanism positioned on the handle members which includes a curved rack member attached to one handle member which passes through a slot in the other handle member. A releasable pawl member is provided on the second handle to engage the rack member and provide a means for releasing the ratchet.

U.S. Pat. No. 4,935,027, to Yoon discloses a surgical instrument having a ratchet mechanism positioned between the handle members. A rack member is provided which extends from one handle and passes through a slot in the second handle to lock the handles in place. Pivoting the rack member away from corresponding grooves in the slot will release the ratchet mechanism.

U.S. Pat. No. 4,428,374, to Auburn discloses a surgical instrument having means for positioning and holding the handle members in relation to each other. A rack member is provided on one handle member which extends through a slot in the second handle member in which a releasable pawl mechanism is provided to engage and disengage the rack member.

The novel surgical instrument according to the present invention obviates the disadvantages encountered in the prior an and provides a precise instrument which is easy to manufacture and efficient to use. The present invention eliminates the need for an external locking device and provides for operation and manipulation of the surgical instrument by a single hand and for locking and unlocking the instrument. The novel surgical instrument further enables a surgeon to actuate the locking mechanism from multiple locations on the handle. The instrument locking mechanism of the present invention incorporates many features which are of use to the surgeon during an operation, including a single jaw control mechanism for effecting both jaw closure and locking while maintaining a lightweight construction in an easy to control device in which all of the features may be operated with one hand. Furthermore, the features are positioned so as to provide a maximum line of sight for the surgeon without obstructing the view to the surgical site.

SUMMARY OF THE INVENTION

A surgical instrument according to an embodiment of the present invention includes a housing portion and an endoscopic portion having a proximal end and a distal end, the endoscopic portion including a pair of coaxial members attached at the proximal end to the housing portion. The endoscopic portion also includes an inner rod member slidable within an outer tube member. The endoscopic portion terminates at the distal end in a pair of jaw members disposed in opposing relation and relatively pivotal about a common point between at least an open position and a closed position.

A jaw control mechanism is associated with the housing portion, and includes at least one actuating member movably mounted in the housing portion. The actuation member has at least one gripping portion thereon such that an operator of the instrument can better manipulate the actuating member with a single hand.

A linking member is pivotally connected to the actuating member and the inner rod member. A notch portion is disposed on the rod member such that when the actuating member is moved in relation to the housing portion in a first direction to a first position the engaging portion engages the notch, locking the jaws in a closed position.

The surgical instrument also includes means for preventing the inner rod member from moving from the first position whereby coaxial reciprocating forces are created in the inner rod member when the locking means are moved to the first position.

BRIEF DESCRIPTION OF THE DRAWINGS

The foregoing as well as other advantages and features of the present invention will become more readily apparent and may be understood by referring to the following detailed description of illustrative embodiments of the locking mechanism for endoscopic or laparoscopic surgical instruments according to the present invention, taken in conjunction with the accompanying drawings, in which:

FIG. 1 illustrates a perspective side view of a first embodiment of the needle holder of the present invention;

FIG. 2 illustrates an exploded view with parts separated of the embodiment of the needle holder shown in FIG. 1;

FIG. 3 illustrates a partial side view in cross section taken along line 3—3 of FIG. 1 showing the jaw mechanism of the needle holder;

FIG. 4 illustrates the partial side view of FIG. 3 with the jaw mechanism of the needle holder in a closed position;

FIG. 5 illustrates a cross-sectional view of the jaws of FIG. 4 taken along section line 5—5;

FIG. 6 illustrates an cross-sectional end view of the jaws of FIG. 4 taken along section line 6—6;

FIG. 7 illustrates a cross-sectional end view of another embodiment of the jaws of the present invention;

FIG. 8 illustrates a cross-sectional side view of the handle of the embodiment of FIG. 1 taken along section line 8—8 showing the instrument control mechanism in its proximal-most position;

FIG. 9 illustrates a cross-sectional view similar to that of FIG. 8 with the instrument control mechanism in its distal-most position;

FIG. 10 illustrates a cross-sectional end view of the locking mechanism of the instrument of FIG. 8 taken along section line 10—10;

FIG. 11 illustrates a cross-sectional end view of the distal end of the handle of FIG. 9 taken along section line 11—11;

FIG. 12 illustrates a top view of the handle portion of another embodiment of the present invention;

FIG. 13 illustrates a cross-sectional side view of the handle portion of FIG. 12 taken along section line 13—13 with the locking mechanism of the present invention in the locked position;

FIG. 14 illustrates a cross-sectional side view similar to that of FIG. 13 showing the locking mechanism of the present invention in the unlocked position;

FIG. 15 illustrates a cross-sectional end view of the locking mechanism of FIG. 13 taken along section line 15—15;

FIG. 16 illustrates a cross-sectional end view of the distal end of the handle of FIG. 14 taken along section line 16—16;

FIG. 18 illustrates a top view of the handle portion of another embodiment of the present invention;

FIG. 19 illustrates a cross-sectional side view of the handle portion of FIG. 18 taken along section line 19—19;

FIG. 20 illustrates a distal end view looking proximally of the embodiment of the present invention shown in FIG. 19;

FIG. 21 illustrates a cross-sectional end view of the mid-section of the handle of FIG. 19 taken along section line 21—21;

FIG. 26 illustrates a partially cut-away side view of the handle of the instrument of FIG. 24;

FIG. 27 illustrates a cut-away distal end view of the handle of FIG. 26 taken along section line 27—27;

FIG. 28 illustrates a partially cut-away top view of the distal end of the handle of FIG. 26;

FIG. 29 illustrates a cross-sectional view of the locking mechanism of FIG. 28 taken along section line 29—29; and FIG. 30 illustrates a cross-sectional end view of a needle positioned between one embodiment of jaws of the present invention.

DETAILED DESCRIPTION OF THE PREFERRED EMBODIMENTS

Figure 17:
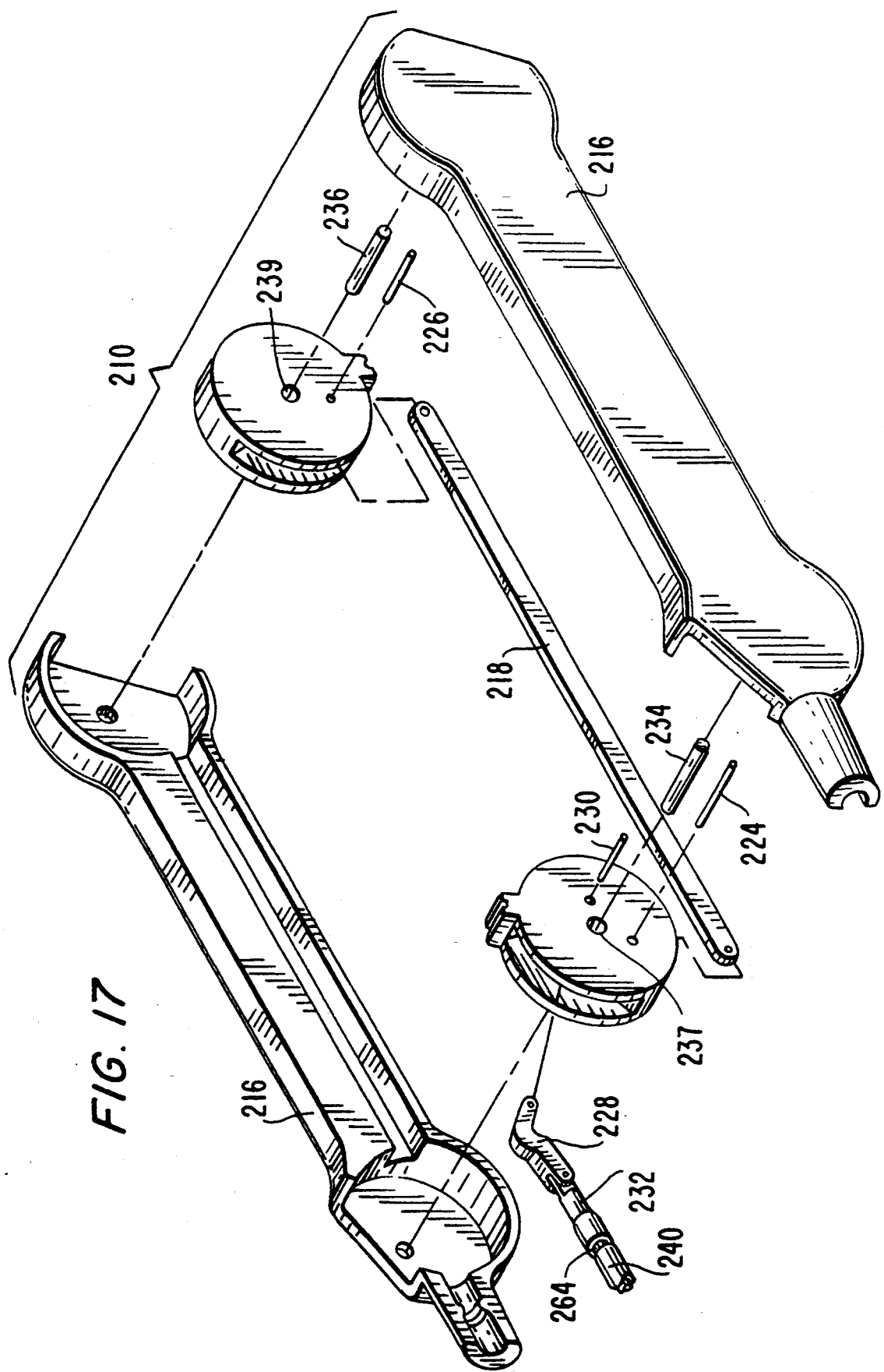
FIG. 17 illustrates an exploded view with separated parts of the handle of FIGS. 12-16.
Figure 22:
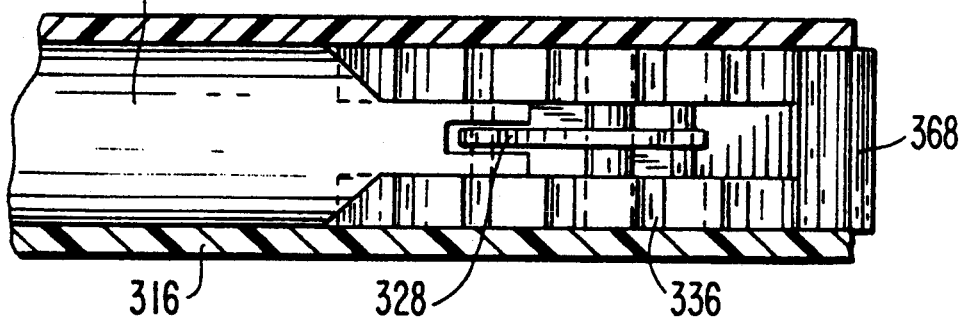
FIG. 22 illustrates a cross-sectional top view of the proximal end of the handle of FIG. 19 taken along section line 22—22.
Figure 23:
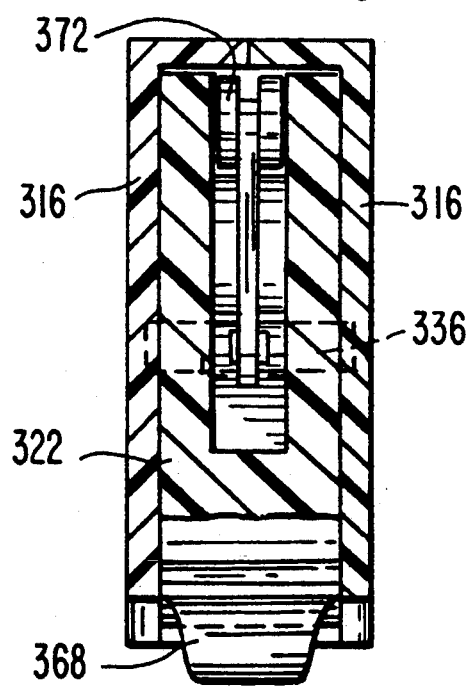
FIG. 23 illustrates a cross-sectional proximal end view of the locking instrument of the handle of FIG. 19 taken along section line 23—23.

Although the following detailed description will focus on several embodiments of surgical instruments used as needle holders, it will become apparent to others having ordinary skill in the art that the locking mechanism discussed hereinafter will be equally useful for other surgical instruments, including but not limited to graspers, forceps, scissors, dissectors, retractors and like instruments. Except where noted otherwise, the materials utilized in the components of the various embodiments of the present invention generally include such materials as polycarbonate for housing sections and related components, and stainless steel for such components which transmit forces. One preferred polycarbonate material is LEXAN brand polycarbonate available from General Electric Company. However, equivalent alternative materials will readily come to the mind of those skilled in the art. First, the description will focus on the structure of one embodiment of the instrument in general. Next, it will concentrate on the structure of the jaw mechanism. The discussion will then describe the operation of the locking mechanism of the present invention and its corresponding interaction with the jaw mechanism. Thereafter, other embodiments of the present invention will be described.

THE INSTRUMENT IN GENERAL

Referring to the embodiment of the invention illustrated in FIGS. 1-11 and initially to FIG. 1 an endoscopic or laparoscopic surgical instrument, for example, laparoscopic needle holder 100 is shown. Generally, needle holder 100 includes handle portion 110, and endoscopic section 112 having at its distal end portion a tool mechanism, one example being the jaw mechanism 114 shown in the open position in FIG. 1. Jaw mechanism 114 is mounted at the distal end portion of endoscopic section 112 such that the jaws open in a vertical plane with respect to the normal holding position of the instrument as shown in FIG. 1. In this manner, a curved surgical needle (not shown) may be grasped such that the needle is positioned transversely between the jaws with its tip and tail portions extending outwardly from either side of the jaws and curving upwardly therefrom. The needle could thereby be moved in the direction of its curvature by a simple twisting of the surgeon's wrist when the instrument is held in the palm of the surgeon's hand with the fingers wrapped around the handle housing.

Referring now to FIG. 2, which shows an exploded perspective view with pans separated, of needle holder 100. Handle portion 110 is comprised of an outer housing preferably formed of separate sections 116 as shown, of polycarbonate material. Separated housing sections 116 shown are optionally attached by fasteners, welding, adhesives, etc. A linking member, such as link bar 118 is pivotally connected to actuating disks 120 and 122 by way of pins 124 and 126. Disks 120 and 122 are preferably of split half construction for ease of assembly of the various interrelated handle components. It is within the scope of the invention, however, that disks 120 and 122 may be formed in a singular piece and the various components attached thereto by way of pins or the like. Disks 120 and 122 are positioned in contoured portion of housing sections 116. The contoured portions may be formed by conventional molding techniques and should be sufficiently deep so as to allow disks 120 and 122 to rotate freely within the formed handle portion 110. Link 128 is pivotally connected at its proximal end to disk 120 by way of pin 130 and at its distal end to inner rod 132 by pin 129. Disks 120 and 122 are positioned and retained in housing sections 116 by interference fitting of pins 134 and 136 in bores 137 and 139 formed in disks 120 and 122. Bores 137 and 139 are preferably located in the center of disks 120 and 122 to facilitate the disks being uniformly rotatable within handle portion 110.

THE JAW MECHANISM

Jaw mechanism 114 will now be described by reference to FIGS. 2-7. Opposing jaws 138 are pivotally attached to endoscopic portion 112 at the distal end of outer tube 140, as best seen in FIG. 3, by way of pin 142. Pin 144 mounts jaws 138 to inner rod 132 through camming slots 146 such that proximal-distal reciprocating motion of inner rod 132 is translated to opening and closing movements of jaws 138.

In FIG. 4, surgical needle 148 is shown in cross-section, positioned transverse to the longitudinal axis of jaws 138 and situated therebetween. Jaws 138 are biased against needle 148 as a result of inner rod 132 being moved to its proximal most position such that pin 144 travels in camming slots 146 biasing jaws 138 against needle 148. Pin 142 provides for the pivoting of jaws 138 with respect to each other and with respect to outer tube 140.

Jaws having various gripping surfaces may be provided on the instrument of the present invention. By way of example, FIGS. 5-7 illustrate two different jaw structures. FIG. 5 shows jaw 150 having a cross-hatched pattern of teeth 152 disposed thereon to provide secure gripping of objects such as needle 148. Teeth 152 may be formed by cutting grooves in jaw member 150 utilizing known machining techniques. With such techniques teeth 150 may be formed of several varying geometries. For example, jaw 150 may be machined or cast to form truncated pyramidal shaped teeth so that teeth of opposing jaw members may abut one another or grip objects with their flattened top surfaces. Alternatively, teeth 150 may be of a more pointed construction such as is illustrated in FIGS. 3, 4 and 6 to create spaced contact points between teeth and the gripped object or tissue as best shown in FIG. 6.

Another possible jaw configuration is illustrated in FIG. 7, wherein jaws 156 have an arcuate cross-section as shown with a longitudinal channel defined by inner wall 156. In this configuration, four points of contact are established as shown at points A-D so that greater stability and control are provided for a curved needle grasped between the opposing jaws.

THE LOCKING MECHANISM

Referring now to FIGS. 8-11, the mechanism for controlling closure and locking of the jaws of the present invention is illustrated therein throughout the several views, in both the locked and unlocked positions. In FIG. 8, a partial cross-section view of the handle 110 of needle holder 100 is shown. Since the left-side housing section is preferably a mirror image of the right-side section, the following discussion of the right-side housing section applies equally to the mirror image left-side and its corresponding components.

Generally, the instrument operating mechanism, which provides for jaw movement and jaw locking control, includes link bar 118 pivotally connected to and disposed between disks 120 and 122, one disk being rotatably mounted in each of the proximal and distal ends respectively, of handle portion 110; and locking link 128 pivotally attached to distal disk 120 and inner rod 132 of endoscopic portion 112. Aside from their connecting pivot points, links 118 and 128 are permitted to move freely about in the interior of handle portion 110. This movement is made possible as a result of channels created between the two joined housing sections. Longitudinal recessed portion 158 is provided in housing section 116 and while being larger in all dimensions than link 118, is preferably contoured to correspond roughly to the shape of link 118 while allowing for some transverse movement of link 118 within handle portion 110 during operation of the instrument. Also, recessed portion 158 is preferably of sufficient depth, i.e., at least slightly greater than one-half the total thickness of link 118, so that when housing sections 116 are joined, link 118 does not contact the bottom of recessed portion 158. Similarly, recessed portions 160 and 162 are formed in each half section of disks 120 and 122 respectively, so that pivotal and translational motion of links 118 and 128 remains unimpeded during operation of the instrument.

Outer tube 140 of endoscopic portion 112 is fixed with respect to handle portion 110 by way of an annular groove cut only partially through outer tube 140 and is fitted into raised rib portion 164 formed in the distal end of each of housing sections 116. Raised ribs 164 could alternatively be formed integrally of section 116 at the time section 116 is molded. In yet another alternative, an annular groove could be cut into section 116 and a washer or O-ring could be fitted therein. This configuration, although preferred, may be reversed so that inner rod 132 is fixed with respect to handle portion 110 and outer tube 140 is pivotally attached to disk 120. Knobs 166 and 168 are provided on disks 120 and 122 respectively to facilitate actuation of the instrument control mechanism and will be discussed in detail below. Alternatively, knobs 166 may be replaced or supplemented by, e.g., knurled surfaces, ribs, etc. provided on either or both of disks 120 and 122.

OPERATION OF THE INSTRUMENT

Referring initially to FIGS. 4 and 8, the operation of instrument will now be described as it is used for grasping objects such as needle 148 between jaws 138, as is shown in FIG. 4. Needle holder 100 is held by the surgeon such that the elongated body of handle portion 110 lies generally transversely in the palm of the surgeon's hand. Due to the symmetry of the handle portion as illustrated and described throughout the drawings and the preceding description, needle holder 100 functions with equal effectiveness when used with either the left hand or the right hand. Furthermore, although the instrument may be controlled using two hands, if so desired, the preferred usage is for a single hand to hold the instrument and control both the closure of jaws 138 as well as locking of the same. For clarity purposes, therefore, since the control of jaw movement and locking thereof may be effected by movement of either knob 166 on disk 120, or knob 168 on disk 120, since movement of one effects a corresponding movement of the other, the operation of needle holder 100 will be described with respect to movement by the surgeon of knob 166 alone. Similar movements of knob 168 will effect similar results with the instrument.

In order to grasp an object such as needle 148, needle holder 100 is positioned such that needle 148 is situated between jaws 138. The surgeon then urges knob 166 in the direction of Arrow E, as illustrated in FIG. 8, which is generally from its distal-most position towards its proximal-most direction. The surgeon preferably accomplishes this rotational motion by applying a force to knob 166 with the thumb of the hand holding the instrument. Since disk 120 is pivotally connected to inner rod 132, the generally proximal movement of knob 166 and, therefore, the rotation of disk 120 in the direction of Arrow E causes inner rod 132 to be drawn in a generally proximal direction. The corresponding proximal movement of pin 144 inserted in the distal end of inner rod 132 and through camming slots 146 of jaws 138 causes the opposing jaws to begin to close. As the surgeon continues to apply a generally proximally directed force to knob 166, jaws 138 eventually contact needle 148 and tensile forces are thus created in inner rod 132. The stretching of the linked components, i.e., disk 120, link 128, inner rod 132 and jaws 138 and the resilience of jaws 138 about needle 148, or with respect to each other, enables the knob 166 to be moved a distance after jaws 132 make contact with needle 148, even if they are closed without an object between them. The surgeon will begin to feel some resistance to further proximal motion when jaws 138 make contact with needle 148. Once knob 166 passes through a mid-point between its distal-most position and its proximal-most position, link 128 begins to travel towards pin 134. Upon further rotational movement of knob 166 by the surgeon, link 128 latches on pin 134 due to notch 170 provided on link 128 and generally located between its proximal and distal ends but preferably nearer its proximal end. Link 128 is thereby situated immediately above and in contact with pin 134 as seen in the cross-section view of FIG. 10. In this position, proximal end of link bar 118 is positioned immediately adjacent the contoured portion formed by recessed portions 162 of each half of disk 122 as best seen in FIG. 11. Jaws 138 are thus locked, thereby grasping needle 148 firmly therebetween.

The surgeon is then free to manipulate the instrument, for example, by turning the wrist of the hand holding the instrument to rotate the needle in order to perform the necessary function at hand, for example, to suture tissue. The needle can be released by reversing the procedures detailed above and moving knob 166 in the direction of Arrow G as shown in FIG. 9. Thereafter, the needle can grasped and regrasped indefinitely as described above to effectuate closure of a wound or the like.

Referring now to the embodiment illustrated in FIGS. 12–17, handle portion 210 of substantially similar endoscopic surgical instrument 200 in both function and structure to instrument 100 is shown.

Needle holder 200 having handle portion 210 is connected to an endoscopic portion 212 which proximal end is partially shown in FIGS. 12–17. Similar to the earlier described handle portion 110, handle portion 210 is constructed of split housing sections 216 having somewhat larger dimensions than housing sections 116, however, link rod 218 is preferably a straight steel rod of rectangular cross-section. (See FIGS. 15 and 16.) This configuration offers increased stability of both the connections at either end of link rod 218 and to the instrument in general. Recessed portions 260 and 262 are contoured to correspond with the straight ends of link rod 218 so that upon operation of the instrument between its full open and full closed positions, link rod 218 is permitted to pivot freely in the space created by the recessed portions 260 and 262 as the split halfs, which make up the construction of disks 220 and 222 respectively, are joined. The operation of instrument 200 is substantially similar to that of instrument 100 and will not be described further at this point.

Another embodiment of the present invention is illustrated in FIGS. 18–23. While the function of instrument is substantially similar to that of instruments 100 and 200, i.e., utilizing a pivoting notched link member and tensile forces to lock a pair of jaws in a closed position, the structure for achieving the function differs somewhat from those other embodiments. That differing structure and the operation thereof will now be discussed. Referring initially to FIG. 18, a similar split half housing construction can be seen for handle portion 310 as was previously described for other embodiments. Housing sections 316 are shown joined to form handle portion 310 with endoscopic portion 312 extending distally outward from the distal end of handle portion 310. A tool mechanism (not shown) such as a jaw mechanism similar to that described above is attached to the distal end of endoscopic portion 312 and operates in similar fashion as previously detailed.

Instead of a distally mounted rotatable disk, such as disk 120 described above, slide bar 372 is provided in a channel formed in housing sections 316, as best seen in FIG. 21, such that slide bar 372 is reciprocally movable between a proximal-most position, when the jaws are in the open position, and a distal-most position (shown in phantom in FIG. 18), when the jaws are in the closed and locked position. Inner rod 332 is pivotally connected directly to link 328 at lower arm 374 which extends distally towards inner rod 332 when link 328 is in the locked position, as illustrated in FIG. 19. Slide bar 372 is pivotally connected, also directly to link 328, however, at an upper distally extending arm 376 thereof, such that link 328 is moved upwardly and distally away from pin 336 to unlock the mechanism and release the jaws or other tool mechanism, upon distal movement of slide bar 372 in the direction of Arrow I as shown in FIG. 19. To provide for ease of operation, slide bar 372 has finger rest 378 protruding from slot 379 formed in the top of handle portion 310 near the distal end thereof. Located at the distal end of finger rest 378, is raised portion 380 which provides a surface to push against, in order to effect distal movement of slide bar 372. Finger rest 378 as well as knob 368 are preferably provided with knurled surfaces to enhance gripping of those surfaces.

The operation of instrument 300 is similar to that of the previously discussed embodiments except that the rotating motion of disk 120, for example, to effect jaw control and locking is replaced by reciprocation of slide bar 372. The operation of locking link 328 is similar to that of, for example, link 128 described above, except that locking link 328 is located in proximally mounted disk 322 instead of being situated in the distal end of housing portion 310.

Figure 24:
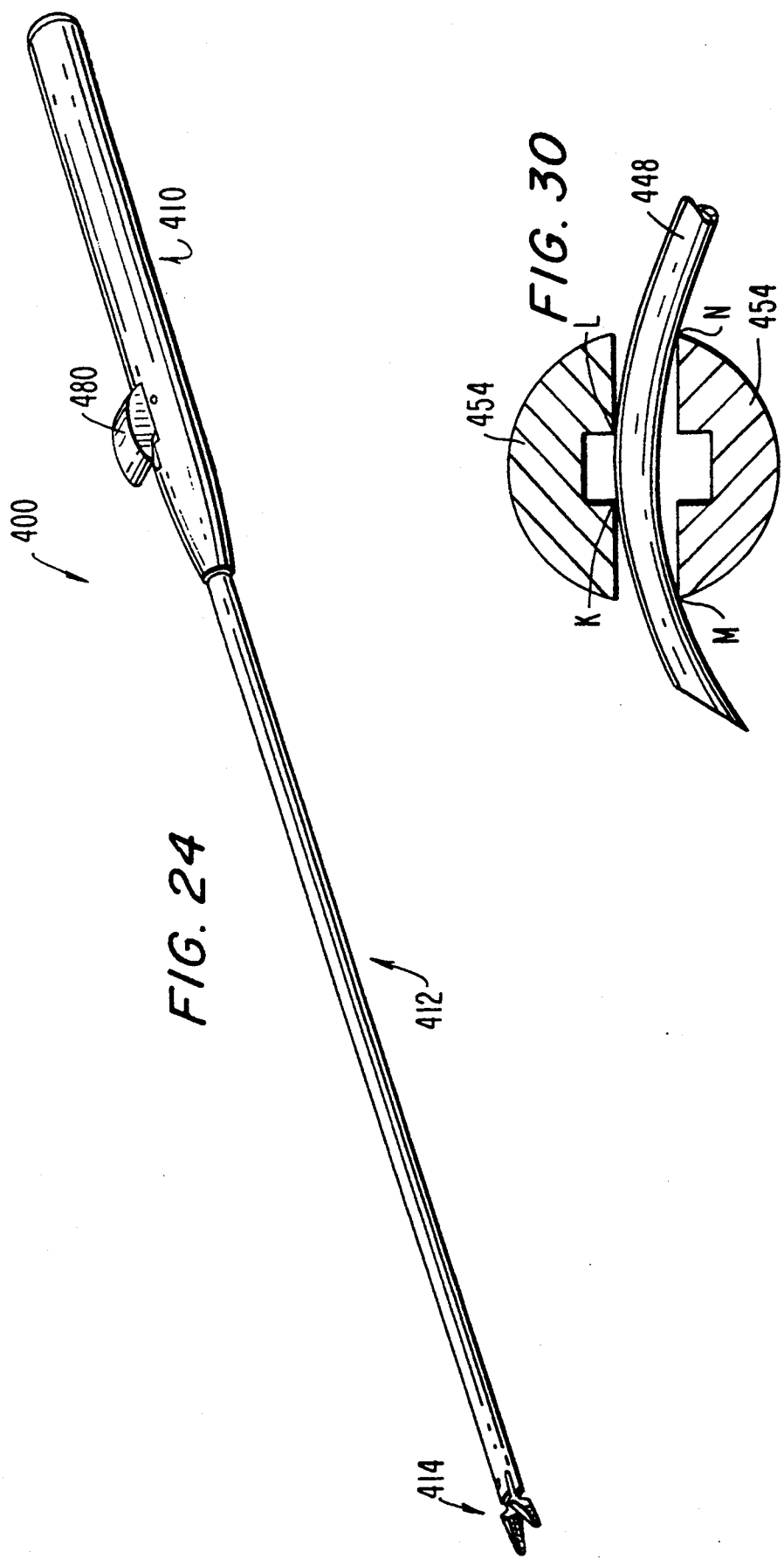
FIG. 24 illustrates a perspective view of another embodiment of a surgical instrument of the present invention.
Figure 25:
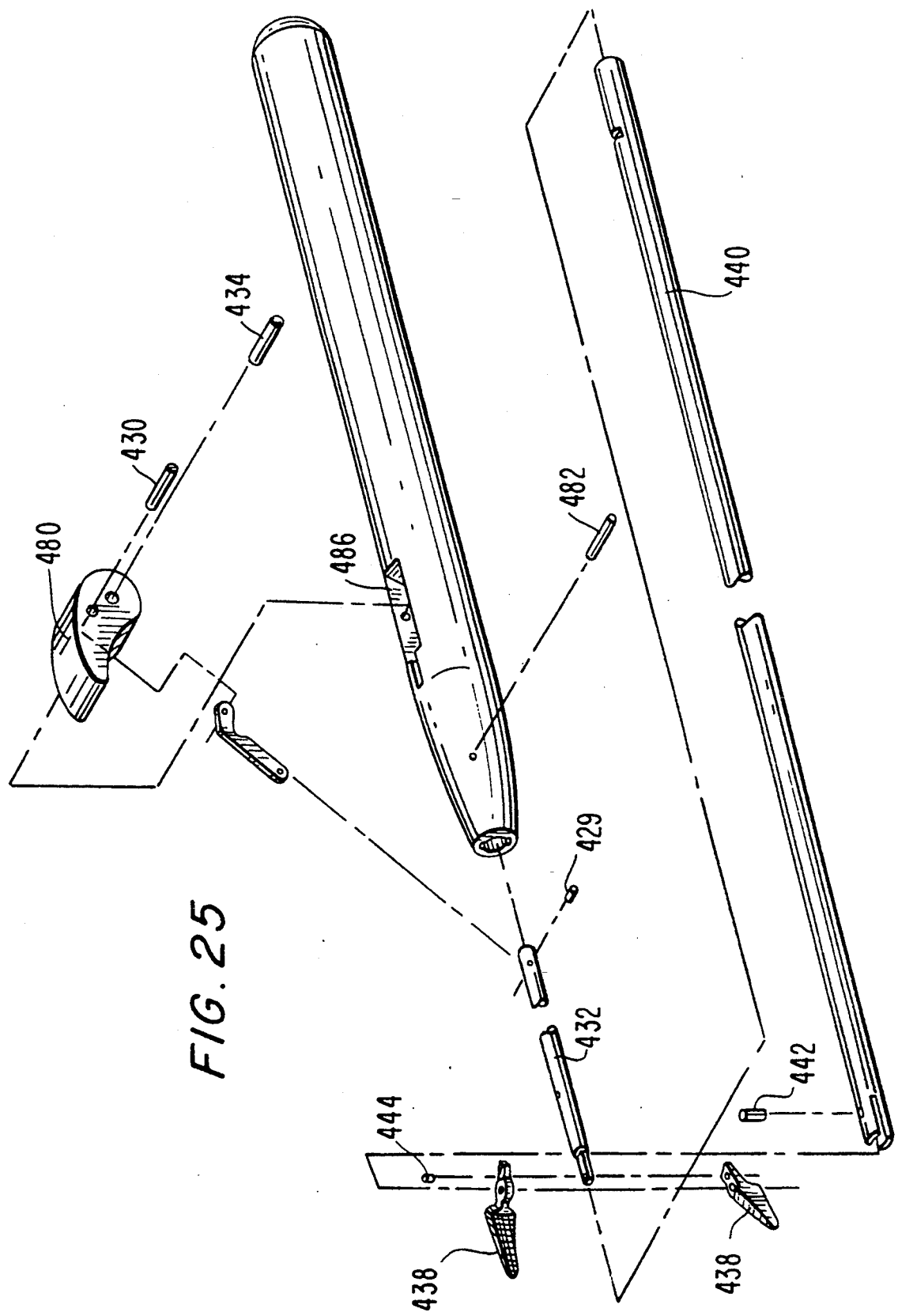
FIG. 25 illustrates an exploded view with parts separated of the instrument of FIG. 24.

Another embodiment of the present invention is illustrated in FIGS. 24–30 as needle holder 400 and will now be discussed in detail. Generally, as shown in FIG. 24, instrument 400 has handle portion 410, endoscopic portion 412 and jaws 414. Handle portion 410 is preferably of split half construction having housing sections 416 joined to form an elongated handle. Endoscopic portion 412 is mounted in the distal end of handle portion 410 by way of pin 482 mounted in a bore formed in handle portion 410 fitting into groove 484 cut partially into the surface of outer tube 440. In such a configuration, outer tube 440 is fixed relative to handle portion 410, while inner rod 432 is movable in a reciprocating manner between proximal most and distal-most positions. Otherwise, both the endoscopic portion and the jaws are identical to those of previously discussed embodiments in structure and operation and will not be discussed further herein other than where necessary.

Referring now to FIGS. 24–27, lever 480 is pivotally mounted by way of pin 434 to handle portion 410 such that lever 480 protrudes from elongated handle portion 410 near the distal end thereof through slot 486 formed therein. Link 428 is pivotally connected to lever 480 by pin 430 and to inner rod 432 by pin 429.

For purposes of a reference point, the following description of the operation of instrument 400 will begin with lever 480 in its distal-most position as shown in FIG. 24 and in phantom in FIG. 26. With lever 480 in its distal-most postition, the jaws are in their fully opened position. The surgeon positions instrument 400 such that the object to be grasped is located between jaws 454. Next, using the thumb of the hand holding instrument 400, the surgeon begins to lift lever 480 and urge it in a generally upward and proximal direction along a path such as is designated by Arrow O in FIG. 26. Link 428 thereby is moved as is illustrated in phantom lines in a generally downward and proximal direction. At approximately the midpoint of the range of movement of lever 480, resistive forces, created by tension, are experienced by the surgeon as described above. Lever 480 is continued to be urged proximally until notch 470 is situated over pin 434 thereby locking the linked components which include: lever 480, link 428, inner rod 432 and the jaws, e.g., jaws 454 shown in FIG. 30 which illustrate the four point contact between needle 448 and jaws 454 at points K,L,M and N which is similar to the illustration in FIG. 7.

While the invention has been particularly shown and described with reference to the preferred embodiments, it will be understood by those skilled in the an that various modifications and changes in form and detail may be made therein without departing from the scope and spirit of the invention. Accordingly, modifications such as those suggested above, but not limited thereto, are to be considered within the scope of the invention.

What is claimed is:

1. A surgical instrument comprising:
   a housing portion;
   an endoscopic portion extending from said housing portion and having a proximal end and a distal end, said endoscopic portion comprising a pair of coaxial members attached at said proximal end to said housing portion, including an inner member slidable within an outer robe member between a first position and a second position, a pair of jaw members extending from a distal end of said endoscopic portion and disposed in opposing relation and relatively pivotal about a common point between at least an open position and a closed position; and
   a jaw control mechanism associated with said housing portion, comprising:
   at least one actuating member movably mounted in said housing portion said at least one acuating member adapted to move said jaw members from a first position to a second position and from said second position to said first position; and
   a linking member pivotally connected to said at least one actuating member and said inner member, said linking member having locking means disposed thereon for locking said linking member with respect to said housing portion such that when said least one actuating member is moved in relation to said housing portion in a first direction to said first position, said inner member becomes locked in said first position and when said at least one actuating member is moved in relation to said housing portion in a second direction to said second position said inner member is movable with respect to said housing portion.

2. A surgical instrument according to claim 1 further comprising means for preventing said inner member from moving from said first position whereby coaxial reciprocating forces are created in said inner member when said at least one actuating member is moved to said first position.

3. A surgical instrument according to claim 1 wherein said at least one actuating member of said jaw control mechanism comprises:
at least one rotatable member pivotally connected to said housing portion.

4. A surgical instrument according to claim 3 wherein said locking means further includes:
a notch portion disposed on said linking member; and
an engaging portion disposed on said actuating member such that when said actuating member is moved in relation to said housing portion in said first direction to said first position said engaging portion engages said notch releasably locking said inner member in said first position.

5. A surgical instrument according to claim 3 wherein said locking means includes a notch disposed between a first end and a second end of said linking member.

6. A surgical instrument according to claim 1 wherein said at least one actuating member of said jaw control mechanism comprises:
a pair of rotatable members pivotally connected to said housing portion; and
a rigid member pivotally connecting said rotatable members such that movement of either of said rotatable members between at least a first position and a second position causes said linking member to move between at least a first position and a second position.

7. A surgical instrument according to claim 6 wherein said locking means includes a notch disposed between a first end and a second end of said linking member.

8. A surgical instrument according to claim 7 wherein at least one of said rotatable members includes means for engaging said notch so that said linking member becomes releasably locked relative to said rotatable member upon movement of said rotatable member to at least one of said first and second positions.

9. A surgical instrument according to claim 8 wherein said engaging means includes a pin member.

10. A surgical instrument according to claim 1 wherein each of said jaw members comprises a gripping surface having a longitudinal channel thereon such that when a curved needle is grasped between said jaw members said needle contacts said jaw members at four points along a surface thereof.

11. A surgical instrument according to claim 1 wherein said at least one actuating member includes at least one gripping portion thereon such that an operator of said instrument can manipulate said instrument and operate said at least one actuating member with a single hand.

12. A surgical instrument according to claim 1 wherein said at least one actuating member includes a surface for enhancing actuation such that said actuating member is readily movable by operator contact along said actuation enhancing surface.

13. A surgical instrument according to claim 1 wherein said at least one actuating member includes a knurled surface such that said actuating member is readily movable by operator contact along said knurled surface.

14. A surgical instrument according to claim 1 wherein each of said jaw members comprises a gripping surface having a plurality of rows of teeth disposed thereon.

15. A surgical instrument according to claim 14 wherein said rows of teeth are oriented diagonal to a longitudinal axis of said jaw members.

16. A surgical instrument comprising:
a housing portion;
an endoscopic portion extending from said housing portion and having a proximal end and a distal end, said endoscopic portion comprising a pair of coaxial members attached at said proximal end to said housing portion, including an inner member slidable within an outer tube member between a first position and a second position, a pair of jaw members extending from a distal end of said endoscopic portion and disposed in opposing relation and relatively pivotal about a common point between at least an open position and a closed position; and
at least one rotatable jaw control means associated with said housing portion and operably connected to at least one of said inner member and said outer tube member for controlling opening and closure of said jaw members, said at least one rotatable jaw control means being movable from a first position to a second position to open said jaw members and from said second position to said first position to close said jaw members.

17. A surgical instrument according to claim 16 further comprising locking means for releasably locking said jaw members in a fixed position.

18. A surgical instrument according to claim 17 wherein said locking means includes a linking member pivotally connected to said at least one rotatable jaw control means and said inner member, said linking member having retaining means disposed thereon for retaining said inner member such that upon movement of said at least one rotatable jaw control means to either said first position or said second position said retaining means releasably retains said inner member.

19. A surgical instrument according to claim 18 wherein said a least one rotatable jaw control means is movable in relation to said housing portion in a first direction to said first position such that said inner member becomes releasably locked and said at least one rotatable jaw control means is movable in relation to said housing portion in a second direction to said second position such that said inner member is movable with respect to said housing portion.

20. A surgical instrument according to claim 16 further comprising a pair of rotatable jaw closure control means operably connected to said inner and outer members for controlling closure of said jaw members such that an operator of said instrument may control closure of said jaw members by movement of either of said rotatable jaw closure control means.

21. A surgical instrument comprising:
a handle;

an outer tube member extending from a distal end of said handle, said outer tube member having an inner member coaxially slidable therein;

a tool mechanism operatively secured at a distal end of said outer tube member, an elongated housing portion associated with said handle; and means, associated with said housing portion for:
(a) controlling movement of said tool mechanism between a first position and a second position; and
(b) locking said tool mechanism, said controlling and locking means being movable to a first position in a first direction to releasably lock said tool mechanism and movable in a second direction to a second position to release said tool mechanism;

wherein said controlling and locking means includes an actuation member adapted to move said controlling and locking means from said first position to said second position and from said second position to said first position.

22. A surgical instrument according to claim 21 wherein said actuation member for said controlling and locking means includes a lever pivotally connected to said housing portion and movable between at least a first position and a second position; wherein said controlling and locking means further includes a linking member pivotally connected to said lever and said inner member, said linking member having means disposed thereon for releasably maintaining said linking member with respect to said handle portion such that said inner member becomes fixed relative to said handle portion upon movement of said lever to at least one of said first and second positions.

23. A surgical instrument according to claim 22 wherein said linking member includes a notch disposed between a first end and a second end thereof.

24. A surgical instrument according to claim 23 wherein said lever includes means for engaging said notch so that said linking member engages said lever upon movement of said lever to at least one of said first and second positions to releasably maintain said lever thereat.

25. A surgical instrument according to claim 22 wherein said actuating member is at least partially disposed within said housing portion; and
further wherein said controlling and locking means further includes a linking member pivotally connected to said actuating member and said inner member, said linking member having means disposed thereon for releasably maintaining said linking member with respect to said housing portion such that said inner member becomes releasably locked in said first position.

26. A surgical instrument according to claim 25 wherein said actuating member is a slidable member.

27. A surgical instrument according to claim 25 wherein said releasable maintaining means includes a notch disposed between a first end and a second end of said linking member.

28. A surgical instrument according to claim 27 wherein said lever includes means for engaging said notch of said linking member upon movement of said lever to at least one of said first and second positions to releasably maintain said linking member thereat.

29. A surgical instrument according to claim 25 further comprising at least one rotatable member pivotally connected to said housing portion and said linking member such that movement of either said at least one rotatable member or said actuating member between at least a first position and a second position causes said linking member to move between at least a first position and a second position.

30. A surgical instrument comprising:
a housing portion;
an endoscopic portion extending from said housing portion and having a proximal end and a distal end, said endoscopic portion comprising a pair of coaxial members attached at said proximal end to said housing portion, including an inner member slidable within an outer tube member between a first position and a second position, a tool mechanism movable between at least a first orientation and a second orientation and opera associated with said inner and outer members and extending from a distal end of said endoscopic portion; and
tool mechanism control means associated with said housing portion, comprising:
first actuating means associated with said housing portion for actuating said tool mechanism, said first actuating means being movable between a first position and a second position;
second actuating means associated with said housing portion actuating said tool mechanism, said second actuating means being movable between a firs position and a second position; and
linking means for operably linking said inner member to each of said first and second actuating means, such that said tool mechanism is operable between first orientation and said second orientation upon actuation of either said first or said second actuation means.

31. A surgical instrument according to claim 30 wherein said linking means includes a latch portion such that upon movement of either of said first or said second actuation means from said respective first positions to said second positions, said inner member becomes releasably locked.

32. A surgical instrument according to claim 30 wherein said tool mechanism includes a pair of jaw members extending from a distal end of said endoscopic portion and disposed in opposing relation and relatively pivotal about a common point between at least an open position and a closed position.

33. A locking mechanism for a surgical instrument which instrument includes a handle portion, a body assembly secured to said handle portion, a tool mechanism secured at a distal end of said body assembly, said body assembly having an inner member slidable within an outer tube member, the locking mechanism comprising:
first actuating means associated with said handle portion for actual said locking mechanism between a locked position and a released position, said first actuating means being movable between a first position and a second position to move said locking mechanism between said locked and released positions;
second actuating means associated with said handle portion for actuating said locking mechanism, said second actuating means being movable between a first position and a second position to move said locking mechanism between said locked and released positions; and linking means associated with said handle portion for operably linking said inner member to each of said first and second actuating means, such that upon movement of either of said first or said second actuation means from said respective first positions to said second positions, said inner member becomes releasably locked.

34. A locking mechanism for a surgical instrument according to claim 33 further including:
a latch portion disposed on said linking member; and
cooperating means associated with said handle portion for cooperating with said latch portion of said linking means.

35. A locking mechanism for a surgical instrument which instrument includes a handle portion, a body assembly secured to said handle portion, a tool mechanism operable between at least a first orientation and a second orientation and secured at a distal end of said body assembly, said body assembly having an inner member slidable within an outer tube member, the locking mechanism comprising:
first means associated with said handle portion for actuating said tool mechanism between said at least first and second orientations;
a first linking member pivotally connected to said inner member and said first actuating means;
means disposed on said handle portion for cooperating with said linking member, and
means disposed on said linking member for latching said linking member with respect to said cooperating means such that said inner member becomes releasably locked upon movement of said actuating means from a first position to a second position and becomes unlocked upon movement of said actuating means from said second position to said first position.

36. A locking mechanism for a surgical instrument according to claim 35 further comprising:
a second means associated with said handle portion for actuating said locking mechanism; and
a connecting rod member connecting said first and said second actuating means such that said first actuating means and said second actuating means are operable by a single hand.

37. A surgical instrument comprising:
a handle portion;
an endoscopic portion having a proximal end and a distal end, said endoscopic portion comprising a pair of coaxial members attached at said proximal end to said handle portion, said endoscopic portion including an inner member slidable within an outer tube member and terminating at said distal end in a tool mechanism, said tool mechanism being operable between at least a first orientation and a second orientation;
locking means including an actuating member, associated with said handle portion, for preventing movement of said tool mechanism between said at least first and second orientations wherein said actuating member of said locking means is movable from a first position to a second position to lock said tool mechanism and from said second position to said first position to unlock said tool mechanism; and
means associated with said distal end of said endoscopic portion and operably associated with said locking means, for preventing said inner member from moving freely as said locking means is moved from said first position to said second position.

38. A surgical instrument according to claim 37 wherein said actuating member includes a lever pivotally connected to said handle portion and movable between at least a first position and a second position; and
wherein said locking means further includes a linking member pivotally connected to said lever and said inner member, said linking member having means disposed thereon for releasably maintaining said linking member with respect to said handle portion such that said inner member becomes fixed relative to said handle portion upon movement of said lever to at least one of said first and second positions.

39. A surgical instrument according to claim 38 wherein said linking member includes a notch disposed between a first end and a second end thereof.

40. A surgical instrument according to claim 39 wherein said lever means includes means for engaging said notch so that said linking member becomes releasably locked with relation to said lever means upon movement of said lever means to at least one of said first and second positions.

41. A surgical instrument according to claim 37 wherein said actuating member is at least partially disposed within said handle portion; and wherein said locking means further includes
a linking member pivotally connected to said at least one actuating member and said inner member, said linking member having means disposed thereon for releasably maintaining said linking member with respect to said handle portion such that said inner member becomes releasably locked in said first position.

42. A surgical instrument according to claim 41 wherein said locking means further includes a notch disposed between a first end and a second end of said linking member.

43. A surgical instrument according to claim 42 wherein said lining member includes means for engaging said notch so that said linking member is releasably maintained relative to said lever means upon movement of said actuating member to at least one of said first position and said second position.

44. A surgical instrument comprising:
a housing portion;
an endoscopic portion having a proximal end and a distal end, said endoscopic portion comprising a pair of coaxial members attached at said proximal end to said housing potion, including an inner member slidable within an outer tube member between at least a first position and a second position, said endoscopic potion terminating at said distal end in a pair of jaw members disposed in opposing relation and relatively pivotal about a common point between at least an open position and a closed position; and
a jaw control mechanism associated with said housing portion, which includes:
at least one rotatable means mounted in said housing portion for actuating said jaw members such that an operator of said instrument can manipulate said instrument and operate said at least one rotatable means with a single hand from a first position to a second position to move said jaw members from said open position to said closed position and from said second position to said first position to move said jaw members from said closed position to said open position.

45. A surgical instrument according to claim 44 further comprising locking means associated with said housing portion for releasably locking said jaw members.

46. A surgical instrument according to claim 45 wherein said locking means includes a linking member pivotally connected to said rotatable means and said inner member, said linking member having means disposed thereon for releasably locking said linking member with respect to said housing portion such that when said at least one rotatable means is moved in relation to said housing portion to said second position, said jaws become releasably locked in said closed position.

47. A surgical instrument comprising:
a housing portion;
an endoscopic portion extending from said housing portion and having a proximal end and a distal end, said endoscopic portion comprising a pair of coaxial members attached at said proximal end to said housing portion, including an inner member slidable within an outer tube member between a first position and a second position, a tool mechanism movable between at least a first orientation and a second orientation operably associated with said inner and outer members and extending from a distal end of said endoscopic portion; and
tool mechanism control means associated with said housing portion, comprising at least one actuating means mounted in said housing portion and rotatable about an axis transverse to a longitudinal axis of said surgical instrument, between a first position to a second position, for actuating said tool mechanism between said at least first and second orientations, such that an operator of said instrument can manipulate said instrument and operate said at least one actuating means with a single hand by moving said at least one actuating means from said first position to said second position to actuate said tool mechanism to said second orientation and from said second position to said first position to actuate said tool mechanism to said first orientation.

48. A surgical instrument according to claim 47 further comprising locking means associated with said housing portion for releasably locking said tool mechanism.

49. A surgical instrument according to claim 48 wherein said locking means includes a linking member pivotally connected to said rotatable means and said inner member, said linking member having means disposed thereon for releaseably locking said linking member with respect to said housing portion such that when said at least one rotatable means is moved in relation to said housing portion in a first direction to a first position, said tool mechanism becomes releasably locked in said second orientation.

50. A surgical instrument comprising:
a handle portion;
a body assembly secured to said handle portion;
a tool mechanism operable between at least a first orientation and a second orientation extending from a distal end of said body assembly;
rotatable actuating means associated with said handle portion such that said rotatable actuating means are rotatable between a first position and a second position about an axis transverse to a longitudinal axis of said instrument, for actuating said tool mechanism, whereby movement of said actuating means from said first position to said second position actuates said tool mechanism to said second orientation and movement of said actuating mans from said second position to said first position actuates said tool mechanism to said first orientation, such that an operator of said instrument can manipulate said instrument and operate said rotatable actuating means with a single hand.

51. A surgical instrument according to claim 50 wherein said rotatable actuating means includes at least one rotatable actuation member.

52. A surgical instrument according to claim 50 wherein said rotatable actuating means includes a pair of rotatable actuation members mounted within said handle means such that said tool mechanism is operable upon actuation of either of said pair of actuation members.

53. A surgical instrument comprising:
a handle portion;
a body assembly secured to said handle portion;
a pair of jaw members extending from a distal end of said body assembly, said jaw members being operable between a first position and a second position;
rotatable actuating means associated with said handle portion and operable between a first and second position, for actuating said jaw members between said first and second positions, whereby movement of said rotatable actuating means from said first position to said second position moves said jaw members to said second position and movement of said rotatable actuating means from said second position to said first position moves said jaw members to said first position, such that an operator of said instrument can manipulate said instrument and operate said rotatable actuating means with a single hand.

54. A surgical instrument according to claim 53 wherein said rotatable actuating means includes at least one rotatable actuation member.

55. A surgical instrument according to claim 53 wherein said rotatable actuating means includes a pair of rotatable actuation members mounted within said handle portion such that said jaw members are operable upon actuation of either of said pair of actuation members.

* * * * *